United States Patent
Neuber et al.

(10) Patent No.: US 12,213,824 B2
(45) Date of Patent: Feb. 4, 2025

(54) IMAGE RECORDING FACILITY FOR A MEDICAL IMAGING SYSTEM, LIFTING COLUMN AND MODULE SYSTEM FOR PRODUCING A LIFTING COLUMN

(71) Applicant: Siemens Healthineers AG, Forchheim (DE)

(72) Inventors: Wolfgang Neuber, Eschenbach I. D. Opf. (DE); Thomas Dippl, Pressath (DE); Dieter Heinl, Erbendorf (DE); Franz Fuetterer, Puechersreuth (DE); Thomas Kleber, Moosbach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 172 days.

(21) Appl. No.: 18/146,667

(22) Filed: Dec. 27, 2022

(65) Prior Publication Data
US 2023/0200764 A1  Jun. 29, 2023

(30) Foreign Application Priority Data
Dec. 29, 2021 (DE) .................. 10 2021 215 075.6

(51) Int. Cl.
*A61B 6/00* (2024.01)
*A61B 6/04* (2006.01)
*A61B 6/40* (2024.01)

(52) U.S. Cl.
CPC .......... *A61B 6/4458* (2013.01); *A61B 6/0407* (2013.01); *A61B 6/4021* (2013.01); *A61B 6/4476* (2013.01)

(58) Field of Classification Search
CPC ... A61B 6/4458; A61B 6/0407; A61B 6/4021; A61B 6/4476; A61B 6/035; A61B 6/0487; A61B 6/40; A61B 6/42; A61B 6/4429; A61B 6/4435; A61B 6/52; A61B 6/54; F16M 11/046; F16M 11/12; F16M 11/18
See application file for complete search history.

(56) References Cited

U.S. PATENT DOCUMENTS

| | | |
|---|---|---|
| 2019/0046138 A1 | 2/2019 | Dippl et al. |
| 2019/0343470 A1 | 11/2019 | Dippl |
| 2020/0148516 A1 | 5/2020 | Greilinger et al. |

FOREIGN PATENT DOCUMENTS

| | | | |
|---|---|---|---|
| CN | 114587401 A | * | 6/2022 |
| DE | 102016202847 A1 | | 8/2017 |
| DE | 102018207375 A1 | | 11/2019 |
| DE | 102019130562 A1 | | 5/2020 |

* cited by examiner

*Primary Examiner* — Kiho Kim
(74) *Attorney, Agent, or Firm* — Harness, Dickey & Pierce, P.L.C.

(57) ABSTRACT

One or more example embodiments relates to an image recording facility for a medical imaging system including a radiation source configured to emit radiation; a patient table having a tabletop for supporting a patient during image recording; a radiation detector configured to detect the radiation, the radiation detector being in or under the tabletop; a first bearing apparatus of bearing apparatuses bearing the radiation source; and a second bearing apparatus of the bearing apparatuses bearing the patient table.

20 Claims, 5 Drawing Sheets

ND MODULE SYSTEM FOR
IMAGE RECORDING FACILITY FOR A MEDICAL IMAGING SYSTEM, LIFTING COLUMN AND MODULE SYSTEM FOR PRODUCING A LIFTING COLUMN

CROSS-REFERENCE TO RELATED APPLICATION(S)

The present application claims priority under 35 U.S.C. § 119 to German Patent Application No. 10 2021 215 075.6, filed Dec. 29, 2021, the entire contents of which are incorporated herein by reference.

FIELD

One or more of example embodiments of the present invention relates to an image recording facility for a medical imaging system, comprising a radiation source for the emission of radiation, in particular of X-ray radiation, a patient table having a tabletop for supporting the patient during the image recording, a radiation detector, arranged in or under the tabletop, for detecting the radiation, wherein the image recording facility has one bearing apparatus bearing the radiation source and one bearing apparatus bearing the patient table respectively.

Related Art

In order to carry out an image recording in the medical sector, in particular in radiography or fluoroscopy, the patient is conventionally supported or positioned on the patient table, frequently so as to be reclining. The body part to be X-rayed is then radiographed with appropriate radiation, which is generated by the radiation source. The radiation passing through the body of the patient impinges on the radiation detector or image receiver, which is frequently arranged below the patient table in what is known as a detector drawer. An X-ray facility of this kind is known for instance from DE 10 2016 202 847 A1.

A further system for medical imaging by means of radiography or fluoroscopy is known from DE 10 2018 207 375 A1. In this system a patient support is rotatably and height-adjustably displaced on a pedestal. An X-ray tube assembly is supported so as to swivel on a ceiling stand.

SUMMARY

An important aspect in connection with corresponding image recording facilities is that for successful imaging, it is necessary for the radiation source, the body part of the patient to be captured by means of the image recording facilities and the radiation detector to be correctly positioned in relation to each other in accordance with the requirements given for the recording. The radiation source, the body part and the radiation detector are arranged collinearly to each other, and, more precisely, along the radiation direction of the radiation emitted by means of the radiation source. This circumstance uses a corresponding mobility of the radiation source, the patient table and/or the radiation detector.

Example embodiments provide an image recording facility which is improved in this regard.

According to one or more example embodiments, a image recording facility for a medical imaging system includes a radiation source configured to emit radiation; a patient table having a tabletop for supporting a patient during image recording; a radiation detector configured to detect the radiation, the radiation detector being in or under the tabletop; a first bearing apparatus of bearing apparatuses bearing the radiation source; and a second bearing apparatus of the bearing apparatuses bearing the patient table, wherein at least one of the bearing apparatuses is a lifting column, the lifting column including, a lifting carriage moveable along a longitudinal direction of the lifting column by a column linear guide, the radiation source or the patient table being attached to the lifting carriage, and a traction mechanism attached to a base attachment point and the lifting carriage, the traction mechanism is configured to transfer a weight force of the radiation source or a weight force of the patient table to the attachment point, the traction mechanism being around a guide pulley and moveable along the longitudinal direction of the lifting column by an actuator and by a guide pulley linear guide.

According to one or more example embodiments, the traction mechanism is a chain, a belt or a cable.

According to one or more example embodiments, the actuator is an electromechanical spindle drive or a hydraulic cylinder drive, the actuator being connected to the guide pulley linear guide.

According to one or more example embodiments, an image recording facility for a medical imaging system includes a radiation source configured to emit radiation; a patient table having a tabletop for supporting a patient during image recording; a radiation detector configured to detect the radiation, the radiation detector being in or under the tabletop; a first bearing apparatus of bearing apparatuses bearing the radiation source; and a second bearing apparatus of the bearing apparatuses bearing the patient table, wherein at least one of the bearing apparatuses is a lifting column, the lifting column including, a lifting carriage moveable along a longitudinal direction of the column by a column linear guide, the radiation source or the patient table being attached to the lifting carriage, the lifting carriage including a first guide wheel and a second guide wheel, and a traction mechanism attached to a base attachment point and to a top attachment point, the traction mechanism being around the first guide wheel and the second guide wheel, wherein at least one of the first guide wheel or the second guide wheel is rotationally drivable along the longitudinal direction of the lifting column by an actuator attached to the lifting carriage in order to move the lifting carriage.

According to one or more example embodiments, the traction mechanism is a chain, the chain meshing with at least one of the first guide wheel or the second guide wheel.

According to one or more example embodiments, the actuator is an electric motor, the electric motor connected to at least one of the first guide wheel or the second guide wheel.

According to one or more example embodiments, a part of the lifting carriage is inside a housing-like bearing structure and another part of the lifting carriage projects outwards through a slit-like opening of the bearing structure running, the slit-like opening along the longitudinal direction of the lifting column.

According to one or more example embodiments, the column linear guide is attached to the bearing structure or is a part of the bearing structure.

According to one or more example embodiments, the radiation source or the patient table is attached to the lifting carriage via a connecting piece forming a tilt joint, wherein the radiation source or the patient table is tiltable about a tilt axis running perpendicular to the longitudinal direction of the lifting column by the tilt joint.

According to one or more example embodiments, the radiation source or the patient table is attached to the lifting carriage via the connecting piece, the connecting piece forming a swivel joint, wherein the radiation source or the patient table can swivel about a swivel axis running perpendicular to the longitudinal direction of the lifting column and perpendicular to the tilt axis by the swivel joint.

According to one or more example embodiments, the radiation source or the patient table is attached to the lifting carriage via the connecting piece or a connecting piece forming a connecting linear guide, wherein the radiation source or the patient table is moveable horizontally away from a bearing structure and towards the bearing structure by the connecting linear guide.

According to one or more example embodiments, the radiation detector is moveable longitudinally and transversely along a table plane of the tabletop, and the radiation source is at least one of (i) moveable with respect to at least a horizontal direction or (ii) can swivel around at least a horizontal axis.

According to one or more example embodiments, the lifting column is attached at the base to a section secured to the floor via a column joint, wherein the lifting column can swivel about a horizontal axis by a column joint.

According to one or more example embodiments, the radiation source or the patient table is directly attachable to the lifting carriage or attachable to the lifting carriage via a connecting piece.

According to one or more example embodiments, A module system configured to produce a lifting column according to one or more example embodiments includes a plurality of bearing structures; a plurality of actuators; a plurality of traction mechanisms; and a plurality of lifting carriages having identical lifting carriage interfaces.

According to one or more example embodiments, at least one of (i) at least two of the plurality of actuators have a different operating capacity, (ii) at least two of the plurality of traction mechanisms have different parameters with respect to mechanical strength, or (iii) at least two connecting pieces are different with respect to at least one of a tilting capacity, swiveling capacity, or displaceability via the respective connecting piece.

BRIEF DESCRIPTION OF THE DRAWINGS

Advantages, details and features of the invention emerge on the basis of the exemplary embodiments explained below and on the basis of the figures. Schematically in the drawings.

DETAILED DESCRIPTION

Figure 1:
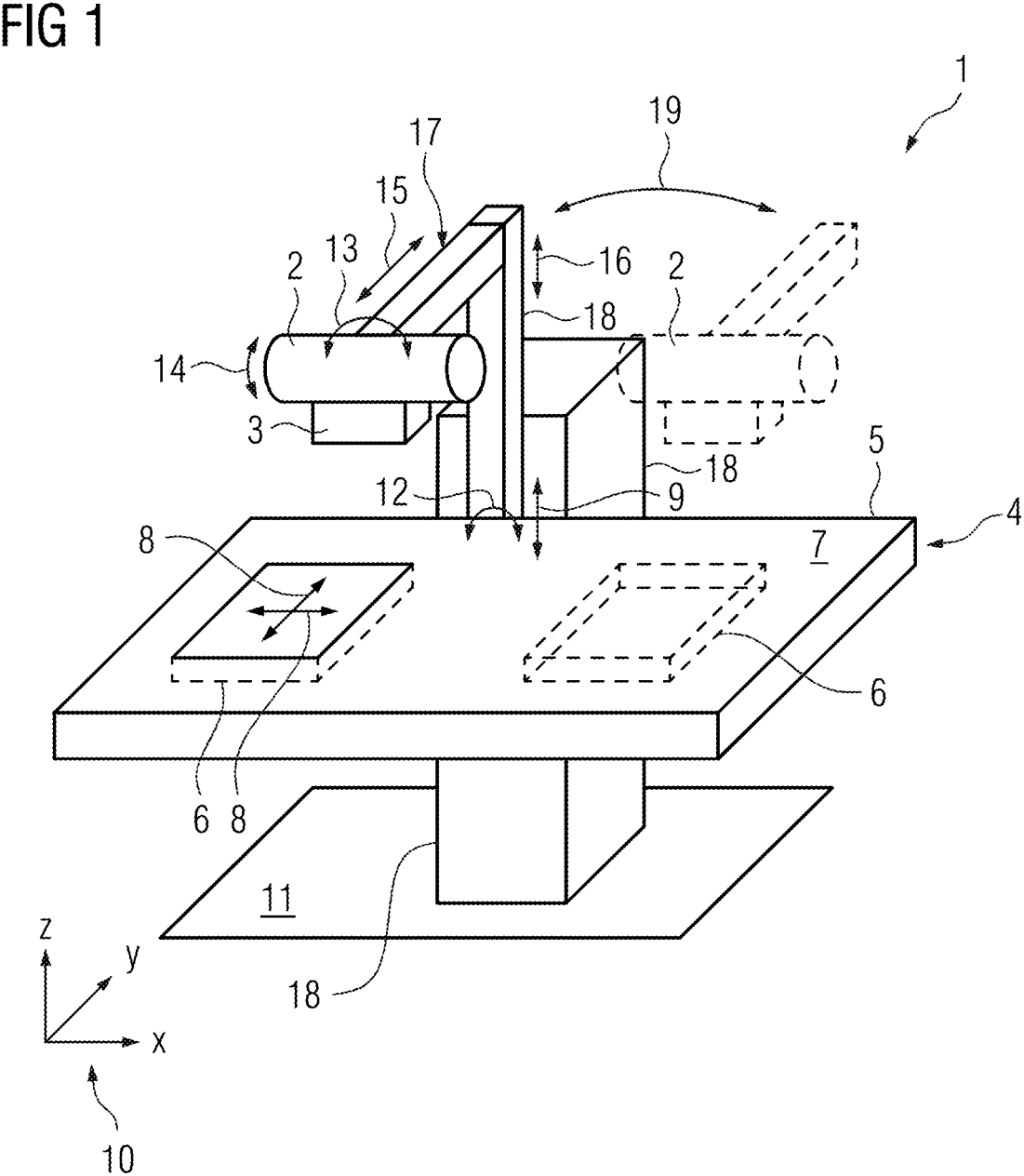
FIG. 1 shows an exemplary embodiment of an inventive image recording facility.

According to one or more example embodiments at least one of the bearing apparatuses is a lifting column, which has a lifting carriage to which the radiation source or the patient table is attached and which can move along a longitudinal direction of the column in or on a column-like bearing structure and by means of a column linear guide, wherein a traction mechanism of the lifting column attached on the one hand to a base attachment point and on the other hand to the lifting carriage is provided, which transfers the weight force of the radiation source or of the patient table to the attachment point and which is led around a guide pulley, which can move along the longitudinal direction of the column by means of an actuator and by means of a guide pulley linear guide.

The lifting column, which can also be referred to as a floor stand, is a pillar-like or supporting foot-like bearing apparatus, to which the radiation source or the patient table is attached. Specifically, the radiation source or the patient table is attached to the lifting carriage, which is in turn arranged along the longitudinal axis of the lifting column so as to move longitudinally on the bearing structure. If the lifting column is attached to the sub-floor or a floor area so as to be in a vertical position, the lifting carriage can be moved along the vertical direction, in other words along the longitudinal direction of the column, wherein a height-adjustability of the lifting carriage and therefore of the radiation source or patient table is achieved. The movement of the lifting carriage is enabled by means of the traction mechanism, the guide pulley and the actuator. The traction mechanism is attached at one of its ends to the lifting carriage for this purpose. At its other end, which opposes the end attached to the lifting carriage, the traction mechanism is attached to a, in respect of the bearing structure, stationary underside or base attachment point. The base attachment point can be provided in the region of a base plate of the lifting column or on the sub-floor or floor area.

Different attachment variants are conceivable for attachment of the ends of the traction mechanism. Screwed or welded connections are thus conceivable for this purpose. In principle, solely a hook arranged on the lifting carriage and/or a hook arranged on the base attachment point, in which a last link of the traction mechanism provided as a chain is suspended, is also conceivable.

The specific arrangement of the traction mechanism will be explained below, without being restricted hereto, for the case in which the lifting column is in a vertical position in the space. The traction mechanism is led, in particular by 180°, around the guide pulley, which is arranged to move longitudinally along the longitudinal direction of the column, and therefore the vertical direction. This means that the traction mechanism, starting from the base attachment point, extends substantially vertically upwards, is led at the top over the guide pulley and then extends substantially vertically downwards, and, more precisely, to the end of the traction mechanism, which is attached to the lifting carriage. The traction mechanism is in a tensioned state owing to the total weight force, which is composed of the weight force of the lifting carriage and the radiation source or the patient table, possibly including the patient, and owing to the degree of freedom of movement of the lifting carriage in the vertical or longitudinal direction of the column. Ultimately the weight force acts on the base attachment point as an upwardly directed tensile force owing to the hoist formed by the traction mechanism and the guide pulley.

The guide pulley can be moved by means of the actuator along the longitudinal direction of the column, vertically upwards and downwards therefore in the case of a vertical lifting column. It is apparent that an upwards movement of the guide pulley results in an upwards movement of the lifting carriage. A downwards movement of the guide pulley analogously results in a downwards movement of the lifting carriage.

This kinematic coupling causes the vertical path covered by the lifting carriage to be identical to twice the vertical path covered by the linear drive or by the piston of the linear drive. The force acting on the guide pulley and therefore to be overcome by means of the actuator is twice the total weight force.

The traction mechanism can be a chain, a belt or a cable. The guide pulley is preferably mounted rotatably so that optimally friction-free guiding of the traction mechanism along the guide pulley is achieved. It is conceivable, in particular when the traction mechanism is a roller chain, that the guide pulley is permanently mounted in the lifting column in respect of a rotational movement. A cable chain can be arranged on or attached to the traction mechanism, moreover, by way of which chain a cable guide for the mobile lifting carriage is possible.

The actuator can be an electromechanical spindle drive or a hydraulic cylinder drive, which is connected to the guide pulley. A piston of the actuator extendably coupled to the guide pulley can accordingly be extended and retracted along the longitudinal direction of the column from a stationary section of the actuator. The stationary section, in a manner similar to the base attachment point, can be arranged on and attached to a base section of the lifting column or directly to the floor or sub-floor.

Within the context of a second embodiment the abovementioned object is inventively achieved in an image recording facility of the type mentioned in the introduction in that at least one of the bearing apparatuses is a lifting column, which has a lifting carriage to which the radiation source or the patient table is attached and which can move along a longitudinal direction of the column in or on a column-like bearing structure and by means of a column linear guide, wherein a traction mechanism of the lifting column attached on the one hand to a base attachment point and on the other hand to a top attachment point is provided, wherein the traction mechanism is led around a first guide wheel and around a second guide wheel of the lifting carriage, wherein the first guide wheel and/or the second guide wheel can be rotationally driven along the longitudinal direction of the column by means of an actuator attached to the lifting carriage in order to move the lifting carriage.

The aspects and features described in respect of the first embodiment similarly apply to the second embodiment if they do not explicitly differ. This applies in particular to the radiation source, the patient table, the radiation detector and the lifting carriage.

In respect of the traction mechanism it is provided in the second embodiment that it is attached at a top attachment point and at a base attachment point. In contrast to the first embodiment, it is not just the end of the traction mechanism attached to the base attachment point, but the two ends which are stationarily provided in respect of the bearing structure in the second embodiment of the image recording facility.

The specific arrangement of the traction mechanism will be explained below, without being limited hereto, for the case where the lifting column is in a vertical position in the space. Starting from the base attachment point of the traction mechanism, which can be provided on a base plate of the lifting column, the traction mechanism extends substantially vertically upwards and is led at the top over one of the guide wheels, for instance over the first guide wheel, in particular by 180°. The traction mechanism then extends substantially vertically downwards, and, more precisely, along the lifting carriage and to the other guide wheel, for instance the second guide wheel. The traction mechanism is then also led around this, in particular by 180°, and then extends substantially vertically upwards to the top attachment point, which can be provided on a cover plate upwardly terminating the lifting column. That which was stated within the context of the first embodiment similarly applies in respect of attachment of the ends of the traction mechanism to the base and top attachment points.

At least one of the guide wheels or both guide wheels can be driven by means of the actuator. On the basis that a sufficiently large static friction or a positive fit present in the context of teeth exists between the guide wheel or the guide wheels and the traction mechanism, slippage between these components is avoided. Consequently, a rotational movement of the guide wheel or guide wheels caused by means of the actuator causes the lifting carriage to move along the longitudinal direction of the column or vertically upwards or downwards, depending on the direction of rotation. Preferably, only one of the guide wheels can be driven by means of the actuator, with the other guide wheel being mounted to freely rotate.

The traction mechanism can be a chain, which meshes in teeth of the first guide wheel and/or of the second guide wheel, in particular both guide wheels. The guide wheels can have different or identical diameters.

The actuator is attached to the lifting carriage and together with it moves along the longitudinal or vertical direction of the column. The actuator can be attached to the lifting carriage by means of a screw connection or a welded joint. Preferably, the actuator is an electric motor, which is connected to the first guide wheel and/or the second guide wheel. This connection can be such that a rotational movement generated by means of the electric motor is transferred 1:1 to the respective guide wheel. It is also conceivable for a gearing to be connected between the electric motor and the guide wheel, which gearing achieves a transmission ratio different from 1:1 in the corresponding transfer of movement.

A cable chain attached on the one hand to the electric motor or to the lifting carriage and on the other hand to a stationary section of the lifting column can be provided in respect of the power supply of the electric motor and/or the cable guide for the lifting carriage.

The optional features, aspects and advantages explained below apply to both the first and the second embodiments.

It is conceivable for part of the lifting carriage to be arranged inside the housing-like bearing structure and for another part of the lifting carriage to outwardly project through a slit-like opening of the bearing structure running along the longitudinal direction of the column. Although the bearing structure can also be frame- or scaffold-like, a housing-like bearing structure is preferred. Housing-like means that the bearing structure has side walls extending in particular along the longitudinal direction of the column, which walls can have recesses, for instance for reasons of weight reduction. In particular, the bearing structure is rectangular, in particular square, preferably with rounded edges, when viewed in cross-section. The bearing structure can be produced from an endless section, in particular from an extruded section.

The slit-like opening can be provided in the side wall extending in the longitudinal direction of the column, through which the lifting carriage extends from inside to outside. In other words, part of the lifting carriage can be arranged in an interior of the lifting column formed by the bearing structure, with another part of the lifting carriage being arranged outside of the bearing structure. In addition, the actuator, the traction mechanism and the guide pulley or the guide wheels can also be arranged in the interior, with the patient table or the radiation source being attached to the section of the lifting carriage arranged outside of the bearing structure.

The column linear guide can be rail-like, be designed as at least one rail or comprise at least one rail, therefore. The column linear guide can comprise in particular two rails running parallel to each other and extending along the longitudinal direction of the column, or have these rails. The one or two rail(s), together with a guide section of the lifting carriage, form a positive fit enabling the linear movement of the lifting carriage. The rail-like column linear guide can be attached to the bearing structure or be designed as part of the bearing structure.

The explanations given in connection with the column linear guide similarly apply to the guide pulley linear guide in respect of the first embodiment of the inventive image recording facility.

In the inventive image recording facility it can be provided that the radiation source or the patient table is attached to the lifting carriage via a connecting piece that forms a tilt joint, wherein the radiation source or the patient table can be tilted about a tilt axis running perpendicular to the longitudinal direction of the column by means of the tilt joint. In an advantageous development it can be provided that the radiation source or the patient table is attached to the lifting carriage via the connecting piece forming a swivel joint, wherein the radiation source or the patient table can swivel about a swivel axis running perpendicular to the longitudinal direction of the column and perpendicular to the tilt axis by means of the swivel joint. An electromechanical actuator of the connecting piece enabling the corresponding movement can be provided in respect of the swiveling and tilting capacity respectively. The tilting and possibly swiveling capacity makes it possible for the radiation source to be oriented in a desired direction in respect of the irradiation direction of the radiation or for the patient table to be tilted or swiveled forwards and backwards or laterally.

The radiation source or the patient table can be attached to the lifting carriage via the connecting piece or a connecting piece forming a linear guide, wherein the radiation source or the patient table can be moved horizontally away from the bearing structure and towards it by means of the linear guide. This horizontal displaceability achieves a further degree of freedom in respect of the movement or positioning of the patient table or the radiation source. For this purpose, the connecting piece can comprise a linear guide or a telescopic section, to which the radiation source or the patient table is attached.

In particular if both the patient table and the radiation source is borne by a lifting column respectively as described in the present case it is conceivable that the tabletop is immovable in respect of a displacement along its table plane and the radiation detector can move longitudinally and transversely along the table plane, wherein the radiation source is movable and/or can be swiveled about at least one horizontal axis in respect of at least one horizontal direction. An electromechanical actuator can thus be provided in or on the tabletop, by means of which the longitudinal or transverse movement of the radiation detector along the table plane is achieved. Compared in particular with the case where the radiation detector is permanently arranged in or on the tabletop, this embodiment advantageously means that the patient table or the tabletop, along with the patient, does not have to be displaced for positioning of the radiation detector. Instead, solely the radiation detector has to be moved for this purpose in or on the otherwise stationary and possibly only swivelable and/or tiltable tabletop.

To be able to set the relative position, required for recording an image, between the radiation source, the patient and the radiation detector, aside from the mobility of the radiation detector just described, a mobility of the radiation source can be provided, which can be moved accordingly in at least one horizontal direction, namely in addition to the high-low mobility, and/or can swivel about at least one horizontal axis. This mobility of the radiation source is achieved for instance by means of the connecting piece already explained above.

A further degree of freedom of movement can be achieved in the inventive image recording facility in that the lifting column is attached at the base to a section secured to the floor via a column joint, wherein the lifting column can swivel about a horizontal axis by means of the column joint. The present invention therefore also incorporates the case where the lifting column is not positioned perpendicularly or vertically in space but also the case where it is tilted or swiveled about a horizontal axis.

The above-mentioned object is also inventively achieved by means of a lifting column having a lifting carriage, to which a radiation source or a patient table is attached or can be attached and which can move along a longitudinal direction of the column in or on a column-like bearing structure and by means of a column linear guide, wherein a traction mechanism attached on the one hand to a base attachment point and on the other hand to the lifting carriage is provided, which transfers the weight force of the radiation source or of the patient table to the attachment point and is led around a guide pulley, which can move along the longitudinal direction of the column by means of an actuator and by means of a guide pulley linear guide. This lifting column is suitable in particular for use in an image recording facility according to the first embodiment.

The above-mentioned object is also inventively achieved by means of a lifting column having a lifting carriage, to which a radiation source or a patient table is attached or can be attached and which can move along a longitudinal direction of the column in or on a column-like bearing structure and by means of a column linear guide, wherein a traction mechanism attached on the one hand to a base attachment point and on the other hand to a top attachment point is provided, wherein the traction mechanism is led around a first guide wheel and around a second guide wheel of the lifting carriage, wherein the first guide wheel and/or the second guide wheel can be rotationally driven by means of an actuator in order to move the lifting carriage along the longitudinal direction of the column. The lifting column is suitable in particular for use in an image recording facility according to the second embodiment.

All features, aspects and advantages explained in connection with the inventive image recording facility can be applied to the embodiments of the inventive lifting column, and vice versa.

It is thus particularly preferably provided in the inventive image recording facility or the inventive lifting column that the lifting carriage has a lifting carriage interface via which the radiation source or the patient table can be directly attached to the lifting carriage or via which the radiation source or the patient table can be attached to the lifting carriage via a connecting piece to which the radiation source or the patient table is attached. If the radiation source or the patient table can be directly attached to the lifting carriage via the lifting carriage interface, the above-described tilting, swiveling and longitudinal displacement capacity of the radiation source or of the patient table cannot be achieved. Instead, the radiation source or the patient table can be moved upwards or downwards solely by means of the lifting carriage and otherwise has no degrees of freedom of movement. This is expedient in particular when the typically heavy patient table is attached to the lifting carriage, since in this case correspondingly powerfully configured electromagnetic actuators do not have to be present.

If the radiation source or the patient table is attached to the lifting carriage via the connecting piece, the connecting piece can thus be designed in accordance with the above description for achieving the tilting and/or swiveling displacement capacity and/or horizontal longitudinal displaceability or longitudinal displaceability provided within the table plane. The connecting piece can have a connecting piece interface via which it can be connected to the lifting carriage or be attached to it.

The present invention relates, moreover, to a module system for producing a plurality of design variants of a lifting column according to the preceding description. It is inventively provided in this module system that it has a plurality of bearing structures, a plurality of actuators, a plurality of traction mechanisms and a plurality of lifting carriages having identical lifting carriage interfaces. The radiation source or the patient table can be directly attached to the lifting carriage via the lifting carriage interfaces. It is also conceivable for the radiation source or the patient table to be attached not directly via the lifting carriage interfaces but via a connecting piece. The module system preferably also comprises a plurality of connecting pieces. In the inventive module system it is provided that at least two of the actuators and/or at least two of the traction mechanisms and/or at least two of the connecting pieces are different to each other.

The inventive module system allows the inventive lifting column to be implemented as simply and inexpensively as possible in the context of a plurality of different intended applications. Depending on the application-specific requirements, an actuator provided especially for this purpose or a traction mechanism provided for this purpose or a connecting piece provided for this purpose can thus be selected, with the remaining components of the lifting column not necessarily having to be specifically adapted hereto, but able to be standardized parts instead. Advantages also result in connection with serviceability since in the case of failure or a defect of one of the components, this component merely has to be replaced.

Specifically it can be provided that in the inventive module system at least two of the actuators have a different operating capacity. Depending on whether the patient table or the radiation source is to be held or moved by means of the lifting column, different requirements result in respect of the power, which can be provided by means of the respective actuator. If the radiation source, and this typically has a weight in the order of 10 kg, is to be held or moved by means of the lifting column a less powerful actuator is thus sufficient compared to the case where the patient table, which, along with the patient, can have a weight of several 100 kg, has to be held or moved by means of the lifting column.

It can also or alternatively be provided in the module system that at least two of the traction mechanisms have different parameters in respect of their mechanical strength. The different parameters can be implemented by way of different dimensions of the traction mechanism, in particular by way of different material thicknesses and/or by way of different materials used. It is also conceivable that at least two of the traction mechanisms have different lengths.

It is also conceivable that at least two of the lifting carriages of the module system have different parameters in respect of their mechanical strength. The lifting carriages are identical in respect of their geometric external dimensions, so the bearing structures, in or on which the lifting carriage is arranged, can likewise be identical in respect of their cross-section. The different mechanical strengths of the lifting carriages can be achieved in particular by way of different material thicknesses and/or different materials.

It can also or alternatively be provided in the inventive module system that at least two of the connecting pieces are different in respect of a tilting capacity and/or swiveling capacity and/or displaceability achieved by means of the respective connecting piece. A system can thus be achieved by way of a suitable selection of one of the connecting pieces of the module system in which the patient table or the radiation source is only tiltable, only swivelable or only displaceable or is a combination of these. As has been explained already, the lifting carriage interfaces are identical, and this similarly applies to the connecting piece interfaces via which the connecting piece can be connected to the lifting carriage.

It is also conceivable in the inventive module system that two of the bearing structures have a different length. As has been mentioned already, the bearing structure is preferably produced from an endless section, so production of bearing structures of correspondingly different length is easily possible. When the radiation source is to be held by means of the lifting column, typically a larger or higher lifting column is necessary therefore than when the patient table is to be held by means of the lifting column, it being possible to achieve these different sizes of the lifting column by way of bearing structures of different lengths. As already addressed, traction mechanisms of the module system, adapted hereto and having different lengths, can be provided.

FIG. 1 shows an exemplary embodiment of an inventive image recording facility 1 for a medical imaging system. The image recording facility 1 comprises a radiation source 2 having a collimator 3 for the emission of radiation. Specifically, the radiation source 2 is an X-ray source, so corresponding X-ray images can be recorded by means of the medical imaging system. Furthermore, the image recording facility 1 comprises a patient table 4 having a tabletop 5, which serves to support or position a patient (not shown in the figures) during the image recording by means of the imaging system. The image recording facility 1 also comprises a radiation detector 6, arranged on or under the tabletop 5, for detecting the X-ray radiation. The X-ray radiation is detected by means of the radiation detector 6 and provided for further processing by means of the imaging system.

For a better understanding of the explanations that follow, FIG. 1 and further figures show a coordinate system 10, with the x-axis running upwards along a horizontal floor area 11 in the longitudinal direction of the patient table 4, the y-direction along the horizontal floor area 11 in the transverse direction of the patient table 4 and the z-axis in the vertical direction.

The tabletop 5 cannot be displaced along its table plane 7. Instead, the radiation detector 6 can be moved longitudinally and transversely along the table plane 7, and this is indicated by the two positions of the radiation detector 6 in FIG. 1 and by the two arrows 8. For this purpose, an actuator (not shown in the figures) enabling the movement of the radiation detector 6 is provided.

The patient table 4 can be displaced in the high-low direction, in other words in the z-direction, and this is indicated by the arrow 9. The patient table 4 or the tabletop 5 can also be swiveled about a swivel axis, which runs in the transverse direction of the table plane 7 and in particular parallel to the y-axis. This swiveling capacity is indicated by the arrow 12. The displaceability and swiveling capacity make it easy for the patient to climb on the tabletop 5. Details in respect of the specific implementation of these movements will be explained below.

In respect of the radiation source 2 it is provided that it can be displaced, swiveled and tilted in a plurality of directions. The radiation source 2 can thus swivel about a swivel axis running parallel to the y-axis, and this is indicated by the arrow 13. Furthermore, the radiation source 2 can be tilted about a tilt axis running along the x-axis, and this is indicated by the arrow 14. In addition, the radiation source 2 can be moved in the horizontal direction along the y-axis, and this is indicated by the arrow 15. These degrees of freedom of movement of the radiation source 2 are achieved by means of a connecting piece 17, explained in more detail below, to which the radiation source 2 is attached. Finally, the radiation source 2 can be moved in the high-low direction or along the z-axis, and this is indicated by the arrow 16.

In the image recording facility 1 it is provided that both the radiation source 2 and the patient table 4 is borne by means of one lifting column 18 respectively, and these are indicated in FIG. 1 merely schematically. In respect of the lifting column 18 bearing the radiation source 2 it is provided that a bearing structure 21 forming the column shape is attached at the base to a section of the lifting column 18 secured to the floor (not shown) via a column joint, so the lifting column 18, along with the connecting piece 17 and the detector 2, can be swiveled about a horizontal axis, namely about the y-axis. This is indicated in FIG. 1 by the arrow 19 and the two indicated swivel positions of the radiation source 2.

For correct imaging it is necessary in the image recording facility 1 for the X-ray radiation generated by means of the radiation source 2 to impinge on the radiation detector 6, with the patient or the body part of the patient to be mapped having to be arranged in the radiation path of the X-ray radiation, in other words between the radiation source 2 and the radiation detector 6. A longitudinal and/or transverse displacement of the radiation detector 6 requires corresponding tracking of the radiation source 2 therefore in respect of the position and/or direction of irradiation.

A displacement of the radiation detector 6 along the x-axis or the longitudinal direction of the patient table 4 thus makes corresponding tracking of the radiation source 2 necessary. This tracking takes place by the radiation source 2, along with the lifting column 18, being swiveled in accordance with the swivel movement indicated by the arrow 19. A resulting inclined position of the radiation source 2 is compensated by means of a swivel movement about the axis indicated by the arrow 13. The necessary distance from the radiation source 2 to the patient or the radiation detector 6 is set via the tracking indicated by the arrow 16. Although this is not provided in the exemplary embodiment shown, the lifting column 18 can also be moved horizontally along the x-axis instead of the tilt indicated by the arrow 12.

A displacement of the radiation detector 6 along the y-axis or transverse direction of the patient table 4 makes tracking of the radiation source 2 necessary in such a way that the source is longitudinally displaced in the direction indicated by the arrow 15. Instead of or in addition to this linear displacement, it can be provided that the radiation source 2 emits the X-ray radiation in a direction different from the vertical direction or asymmetrically superimposes it in the collimator 3. In addition or alternatively, the radiation source 2 can be correspondingly tracked or set via the tilting movement indicated by means of the arrow 14.

Possible specific exemplary embodiments of the lifting column 18 will be explained below on the basis of FIGS. 2 to 4, which can be combined with each other as desired in respect of the implementation of the degrees of freedom of movement indicated by the arrows 12 to 15 and 17 and 19.

Figure 2:
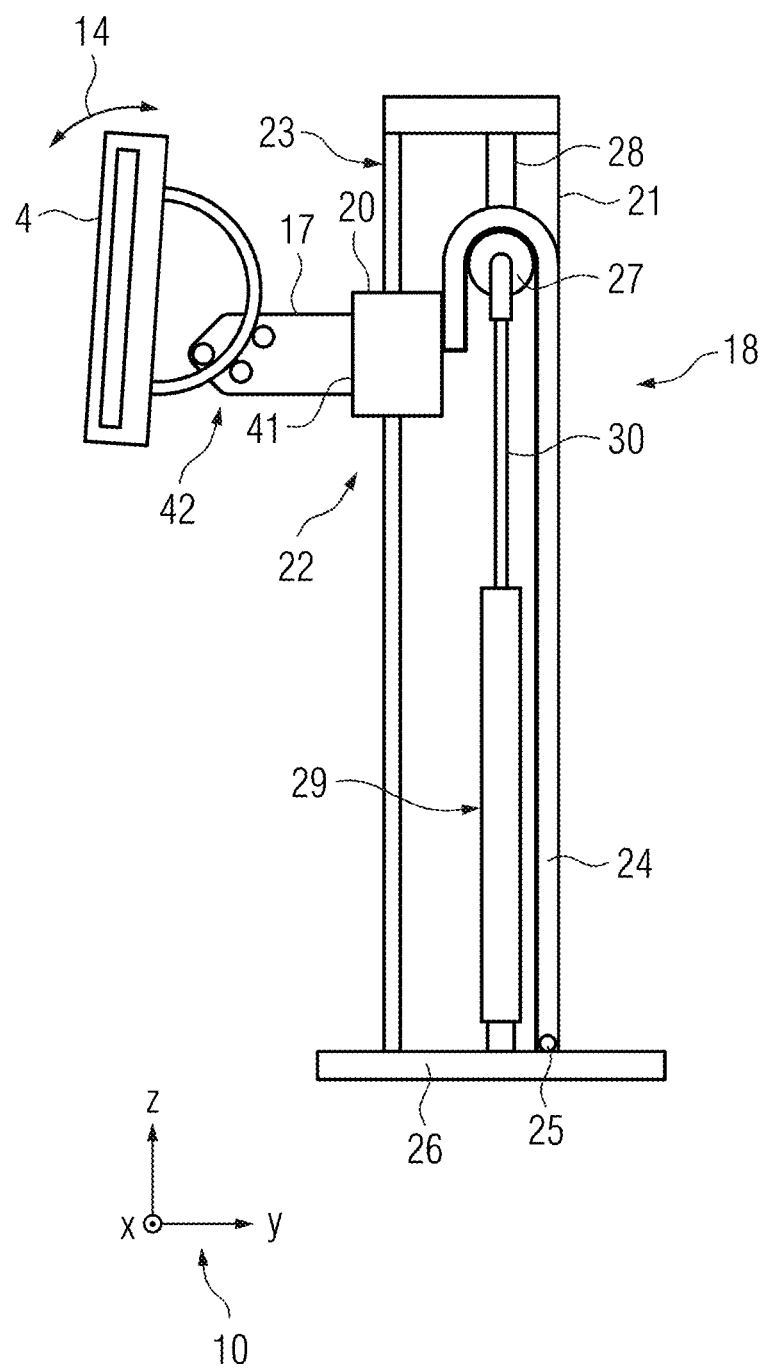
FIG. 2 shows a longitudinal section through a first exemplary embodiment of an inventive lifting column.

FIG. 2 shows a first exemplary embodiment of the lifting column 18, which can be provided in the image recording facility 1 explained on the basis of FIG. 1. Although the patient table 4 is attached to the lifting column 18 in FIG. 2, the radiation source 2 can be attached hereto as an alternative.

The lifting column 18 comprises a lifting carriage 20 to which the patient table 4 is attached, namely via the connecting piece 17. The lifting column 18 also comprises the housing-like, column-like bearing structure 21, with part of the lifting carriage 20 being arranged inside and another part being arranged outside of the bearing structure 21. The lifting column 18 or the bearing structure 21 has for this purpose a slit-like opening 22 running along the longitudinal direction of the column, through which the lifting carriage 20 extends.

In respect of the lifting carriage 20 it is provided that it can move along the longitudinal direction of the column, in other words along the z-axis, by means of a column linear guide 23. Details in respect of the column linear guide 23 will be explained below. The lifting column 18 also comprises a traction mechanism 24, which is attached on the one hand to a base attachment point 25 and on the other hand to the lifting carriage 20. The base attachment point 25 is provided in the region of a base plate 26 of the lifting column 18, with this being attached, in particular screwed, to the floor area 11 via the base plate 26. In respect of the base plate 26 it can also be provided that it is a pre-assembly plate, in other words not a constituent part of the finished column 18. With reference to FIG. 1, the base plate 26 can ultimately correspond to the base section 11.

In the present case, the traction mechanism 24 is a cable, namely made of steel, with it also being possible alternatively for the traction mechanism 24 to be a chain, in particular a roller chain, or a belt. The traction mechanism 24 is led around a guide pulley 27, which in turn can move by means of a guide pulley linear guide 28 along the longitudinal direction of the column or z-axis. The guide pulley 27 is rotatably attached inside the bearing structure 21. Furthermore, the guide pulley 27 is coupled to an actuator 29, which is attached on the one hand to the base plate 26 or the base section 11 and on the other hand is connected to the guide pulley. The guide pulley 27 is displaced by means of the actuator 29 or an extendable piston 30 of the actuator 29 along the longitudinal direction of the column, and, more precisely, along the longitudinal direction of the column predefined by the guide pulley linear guide 28. This displacement of the guide pulley 27 causes a vertical movement of the lifting carriage 20, along with patient table 4. In the exemplary embodiment shown the actuator 29 is an electromechanical spindle drive, but can also be a hydraulic cylinder drive as an alternative.

A cable chain (not shown in more detail in FIG. 2) for implementing a cable guide for the lifting carriage 20 and in particular for supplying electrical energy to an actuator enabling the tilting capacity of the patient table 4 is provided along the traction mechanism 21, moreover.

Figure 3:
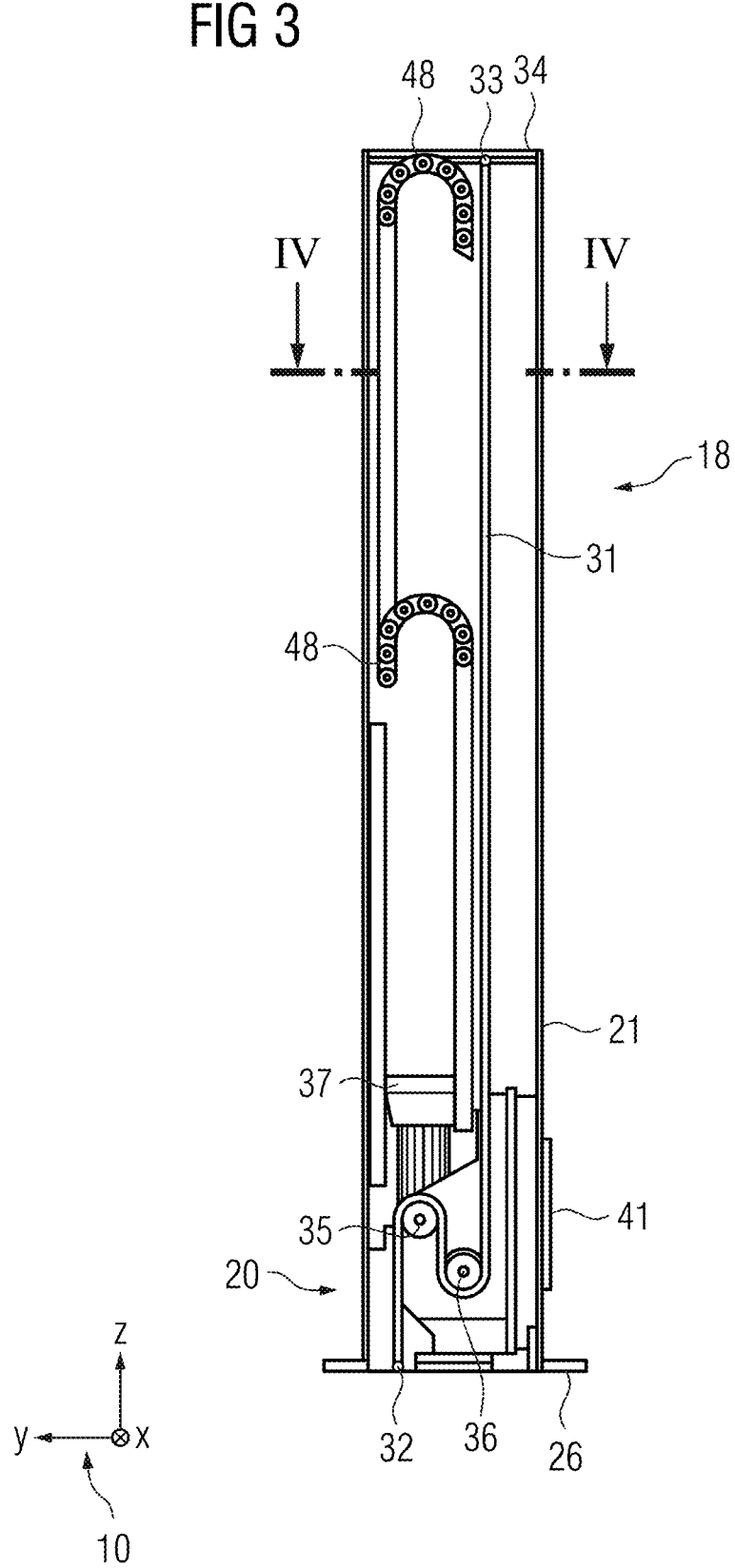
FIG. 3 shows a longitudinal section through a second exemplary embodiment of an inventive lifting column.
Figure 4:
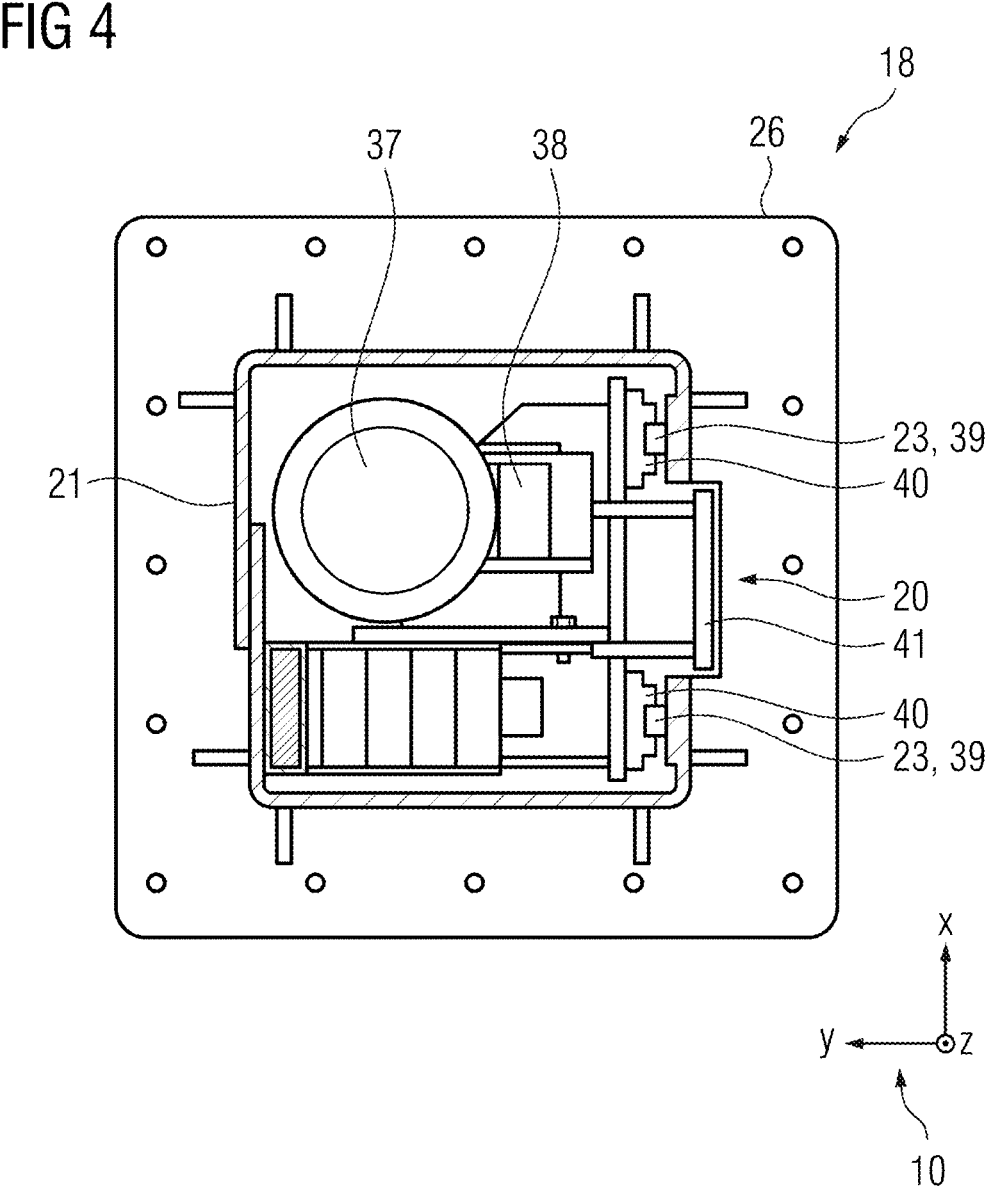
FIG. 4 shows a cross-section through the lifting column of FIG. 3 along the line IV-IV.

Reference will be made below to FIGS. 3 and 4, with the second exemplary embodiment of the inventive lifting column 18 being explained on the basis of these figures, which embodiment can likewise be provided in connection with the image recording facility 1 shown in FIG. 1. FIG. 3 shows a sectional view along the longitudinal direction of the column, and FIG. 4 shows a cross-section of the lifting column 18 along the section line IV-IV shown in FIG. 3. The aspects stated in connection with the lifting column 18 explained on the basis of FIG. 2 similarly apply, if they do not explicitly differ, to the lifting column 18 shown in FIGS. 3 and 4.

The lifting column 18 in FIGS. 3 and 4 comprises a traction mechanism 31, which in the present case is, by way of example, a chain. The traction mechanism 31 is attached on the one hand to a base attachment point 32 and on the other hand to a top attachment point 33. The base attachment point 32 is provided in the region of the base plate 26 or the base section 11 and the top attachment point 33 on a top plate 34 of the lifting column 18. By way of example, the attachment points 32, 33 are formed by means of a hook provided on the base plate 26 and the top plate 34 respectively, in which an end link of the traction mechanism 31 designed as a chain is respectively.

Similar to the exemplary embodiment explained on the basis of FIG. 2, a lifting carriage 20 is also provided in this exemplary embodiment, which can move along the longitudinal direction of the column by means of a column linear guide 23. The traction mechanism 31 is led around a first guide wheel 35 and around a second guide wheel 36, which are arranged on the lifting carriage 20 respectively. The traction mechanism 31 is a chain whose links mesh in teeth of the guide wheels 35, 36. In addition, an actuator 37 attached to the lifting carriage 20 is provided by means of which the second guide wheel 36 can be rotationally driven, with a corresponding rotation of the second guide wheel 36 resulting in a vertical movement of the lifting carriage 20. The actuator 37 is an electric motor, connected to the second guide wheel 36 via a gearing 38, the motor being supplied with current via a cable chain 48, which is shown in FIG. 3 in respect of the highest and lowest positions of the lifting carriage 20.

The aspects explained below apply both to the first embodiment (see FIG. 2) and to the second embodiment (see FIGS. 3 and 4) of the inventive lifting carriage 18. The column linear guide 23 and, in respect of the first embodiment, the guide pulley linear guide 28 is thus configured respectively as a rail guide attached to the bearing structure 21. Details in this regard can be seen in particular in FIG. 4. The column linear guide 23 thus comprises two parallel rails 39 running along the longitudinal direction of the column, which form a corresponding positive fit with guide sections 40 of the lifting carriage 20 designed as guide blocks.

In respect of the lifting carriage 20 it is provided that it has a lifting carriage interface 41 via which the radiation source 2 or the patient table 4 can be attached to the lifting carriage 20. While in FIG. 1 the lifting column 18 is shown in a state in which the patient table 4 is attached to the lifting carriage 20, FIGS. 3 and 4 show a state in which neither the radiation source 2 nor the patient table 4 is attached to the lifting carriage 20.

In principle, it can be provided that the radiation source 2 or the patient table 4 is directly attached to the lifting carriage 20. The radiation source 2 or the patient table 4 has in this case a corresponding radiation source interface or patient table interface, which can be connected to the lifting carriage interface 41. In this case, the radiation source 2 or the patient table 4 is permanently attached to the lifting carriage 20, so the radiation source 2 or the patient table 4 can be displaced solely along the longitudinal direction of the column.

As can be seen in particular on the basis of FIG. 2, the radiation source 2 or the patient table 4 can be attached to the lifting carriage 20 via the connecting piece 17 to which the radiation source 2 or the patient table 4 is attached, in particular detachably. In particular the degrees of freedom of movement, indicated by the arrows 13 to 15 in FIG. 1, of the radiation source 2 or the patient table 4 can be achieved by means of the connecting piece 17. Specifically, it is provided in the connecting piece 17 shown in FIG. 2 that it forms a tilt joint 42.

Figure 5:
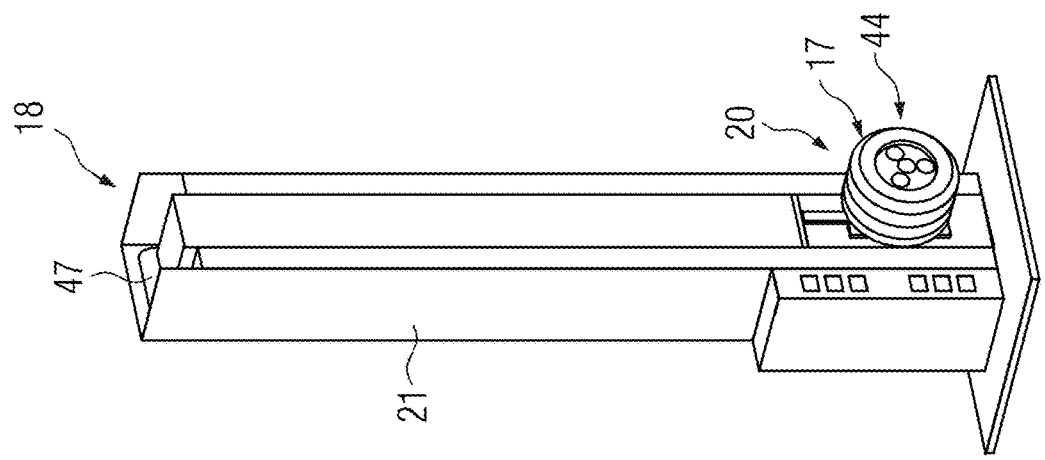
FIG. 5 shows three variants of the lifting column in FIGS. 3 and 4 to explain the inventive module system.
Figure 5:
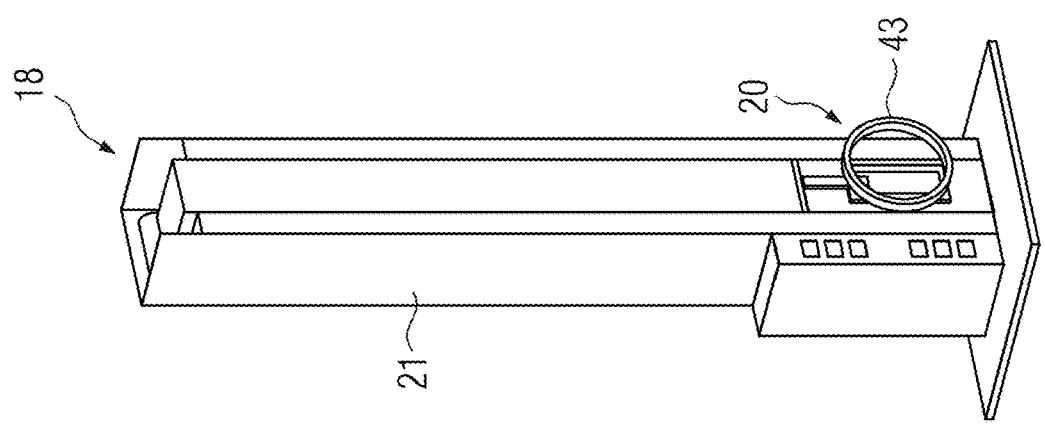
Figure 5:
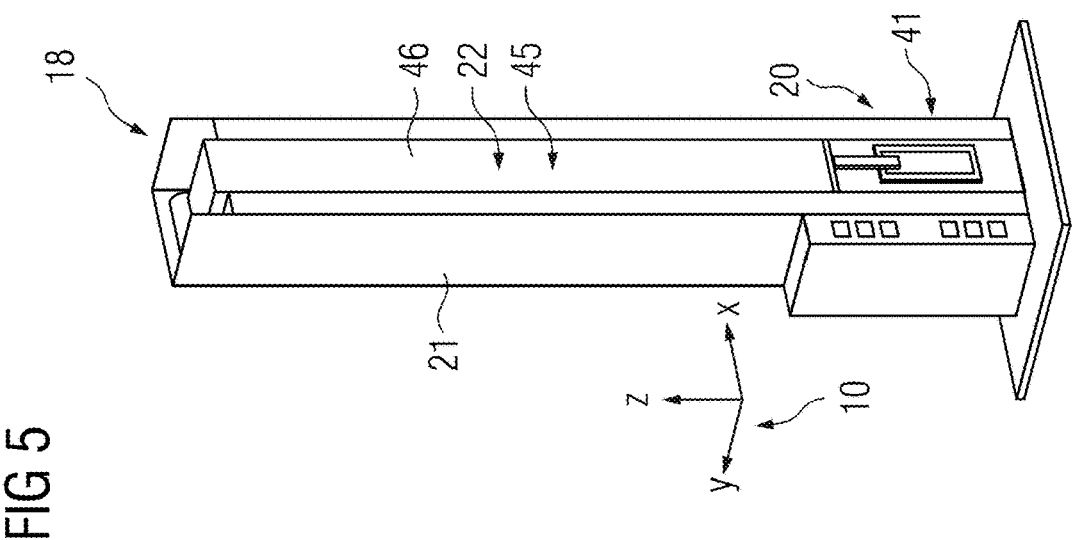

Reference will be made below to FIG. 5, on the basis of which an exemplary embodiment of an inventive module system will be explained. The module system is provided for producing a plurality of different design variants of a lifting column 18 according to the exemplary embodiment shown in FIGS. 3 and 4.

The lifting column 18 represented on the left in FIG. 5 is shown in a state in which the connecting piece 17 is not attached to the lifting carriage 20. The lifting column 18 represented in the middle of FIG. 5 corresponds to the one represented on the left, with a first component of the connecting piece 17, namely a connecting piece interface 43, being provided to which the lifting carriage 20 or its interface 41 is attached. The right of FIG. 5 shows the lifting column 18 in a state in which the complete connecting piece 17 is attached to the lifting carriage interface 41, wherein the radiation source 2 or the patient table 4 is attached to the connecting piece 17. In the exemplary embodiment shown on the right of FIG. 5 the connecting piece 17 comprises a rotary gear, so it ultimately forms a swivel joint 44.

In respect of the module system it is provided that it has a plurality of connecting pieces 17. Each of the connecting pieces 17 has a connecting piece interface 43, which can be connected to the lifting carriage interface 41, such as the interface specifically shown in FIG. 5. The different connecting pieces 17 implement different variants with regard to the degrees of freedom explained on the basis of FIG. 1, in other words in respect of the tilting capacity, swiveling capacity and longitudinal displaceability.

Although this is not explicitly shown on the basis of FIG. 5, for the described module system it is also provided that it has a plurality of bearing structures 21, a plurality of actuators 29, 37, a plurality of traction mechanisms 24, 31 and a plurality of lifting carriages 20 having identical lifting carriage interfaces 41 respectively.

In respect of the actuators 29, 37 it is provided that they have different operating capacities. The different traction mechanisms 24, 31 have different parameters in respect of their mechanical strength. This is achieved by a different material thickness or material selection. The different lifting carriages 20 of the module system differ, in a manner similar to the different traction mechanisms 24, 31, with regard to their mechanical strength. The bearing structures 21 of the module system have different lengths.

Although the components of the module system differ it is possible to combine them with each other or to assemble them on each other for assembly of the corresponding lifting column 18. The module system thus makes it possible to adapt the lifting column 18 to be manufactured specifically to its use-dependent requirements. This relates for instance to mechanical requirements, for instance different weights or masses to be moved by means of the lifting carriage 20, and this can be taken into account by the appropriate selection of suitable actuators 29, 37, traction mechanisms 24, 31 and lifting carriages 20. Furthermore, lifting columns 18 having different heights can be implemented, namely by way of the appropriate selection of a bearing structure 21 having a desired length. A traction mechanism 24, 31 of appropriate length and adapted hereto can be selected.

A further aspect in respect of the exemplary embodiment of the lifting column 18 shown will additionally be explained on the basis of FIG. 5. It is thus provided in respect of the opening 22 that it is or can be closed by way of a blind 45. The blind 45 has a flexible, strip-like material 46 whose width matches the opening 22, and which can be rolled up and unrolled on a roller 47, in particular by means of an elastic spring element. In the present case, rolling up and unrolling take place during the corresponding movement of the lifting carriage 20 along the longitudinal direction of the column in or counter to the elastic restoring force of the spring element.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been described in detail with reference to example embodiments, the present invention is not limited by the disclosed examples from which the skilled person is able to derive other variations without departing from the scope of the invention.

The invention claimed is:

1. An image recording facility for a medical imaging system, comprising:
 a radiation source configured to emit radiation;
 a patient table having a tabletop for supporting a patient during image recording;
 a radiation detector configured to detect the radiation, the radiation detector being in or under the tabletop;
 a first bearing apparatus of bearing apparatuses bearing the radiation source; and
 a second bearing apparatus of the bearing apparatuses bearing the patient table, wherein at least one of the bearing apparatuses is a lifting column, the lifting column including,
  a lifting carriage moveable along a longitudinal direction of the lifting column by a column linear guide, the radiation source or the patient table being attached to the lifting carriage, and
  a traction mechanism attached to a base attachment point and the lifting carriage, the traction mechanism is configured to transfer a weight force of the radiation source or a weight force of the patient table to the attachment point, the traction mechanism being around a guide pulley and moveable along the longitudinal direction of the lifting column by an actuator and by a guide pulley linear guide.

2. The image recording facility of claim 1, wherein the traction mechanism is a chain, a belt or a cable.

3. The image recording facility of claim 1, wherein the actuator is an electromechanical spindle drive or a hydraulic cylinder drive, the actuator being connected to the guide pulley linear guide.

4. A lifting column for use in the image recording facility of claim 1.

5. The lifting column of claim 4, wherein the radiation source or the patient table is directly attachable to the lifting carriage or attachable to the lifting carriage via a connecting piece.

6. A module system configured to produce the lifting column of claim 4, wherein the module system comprises:
 a plurality of bearing structures;
 a plurality of actuators;
 a plurality of traction mechanisms; and
 a plurality of lifting carriages having identical lifting carriage interfaces.

7. The module system as claimed in claim 6, wherein at least one of (i) at least two of the plurality of actuators have a different operating capacity, (ii) at least two of the plurality of traction mechanisms have different parameters with respect to mechanical strength, or (iii) at least two connecting pieces are different with respect to at least one of a tilting capacity, swiveling capacity, or displaceability via the respective connecting piece.

8. An image recording facility for a medical imaging system, comprising:
 a radiation source configured to emit radiation;
 a patient table having a tabletop for supporting a patient during image recording;
 a radiation detector configured to detect the radiation, the radiation detector being in or under the tabletop;
 a first bearing apparatus of bearing apparatuses bearing the radiation source; and
 a second bearing apparatus of the bearing apparatuses bearing the patient table, wherein at least one of the bearing apparatuses is a lifting column, the lifting column including,
  a lifting carriage moveable along a longitudinal direction of the column by a column linear guide, the radiation source or the patient table being attached to the lifting carriage, the lifting carriage including a first guide wheel and a second guide wheel, and
  a traction mechanism attached to a base attachment point and to a top attachment point, the traction mechanism being around the first guide wheel and the second guide wheel, wherein at least one of the first guide wheel or the second guide wheel is rotationally drivable along the longitudinal direction of the lifting column by an actuator attached to the lifting carriage in order to move the lifting carriage.

9. The image recording facility of claim 8, wherein the traction mechanism is a chain, the chain meshing with at least one of the first guide wheel or the second guide wheel.

10. The image recording facility of claim 9, wherein the actuator is an electric motor, the electric motor connected to at least one of the first guide wheel or the second guide wheel.

11. The image recording facility of claim 9, wherein a part of the lifting carriage is inside a housing-like bearing structure and another part of the lifting carriage projects outwards through a slit-like opening of the bearing structure running, the slit-like opening along the longitudinal direction of the lifting column.

12. The image recording facility of claim 8, wherein the actuator is an electric motor, the electric motor connected to at least one of the first guide wheel or the second guide wheel.

13. The image recording facility of claim 8, wherein a part of the lifting carriage is inside a housing-like bearing structure and another part of the lifting carriage projects outwards through a slit-like opening of the bearing structure running, the slit-like opening along the longitudinal direction of the lifting column.

14. The image recording facility of claim 13, wherein the column linear guide is attached to the bearing structure or is a part of the bearing structure.

15. The image recording facility of claim 8, wherein the radiation source or the patient table is attached to the lifting carriage via a connecting piece forming a tilt joint, wherein the radiation source or the patient table is tiltable about a tilt axis running perpendicular to the longitudinal direction of the lifting column by the tilt joint.

16. The image recording facility of claim 15, wherein the radiation source or the patient table is attached to the lifting carriage via the connecting piece, the connecting piece forming a swivel joint, wherein the radiation source or the patient table can swivel about a swivel axis running perpendicular to the longitudinal direction of the lifting column and perpendicular to the tilt axis by the swivel joint.

17. The image recording facility of claim 15, wherein the radiation source or the patient table is attached to the lifting carriage via the connecting piece or a connecting piece forming a connecting linear guide, wherein the radiation source or the patient table is moveable horizontally away from a bearing structure and towards the bearing structure by the connecting linear guide.

18. The image recording facility of claim 8, wherein the radiation detector is moveable longitudinally and transversely along a table plane of the tabletop, and the radiation source is at least one of (i) moveable with respect to at least a horizontal direction or (ii) can swivel around at least a horizontal axis.

19. The image recording facility of claim 8, wherein the lifting column is attached at the base to a section secured to a floor via a column joint, wherein the lifting column can swivel about a horizontal axis by a column joint.

20. A lifting column for use in the image recording facility of claim 8.

* * * * *